United States Patent
De The et al.

(10) Patent No.: US 9,228,998 B2
(45) Date of Patent: Jan. 5, 2016

(54) DRUG MONITORING METHODS USING THE PROMYELOCYTIC LEUKEMIA PROTEIN AS A REDOX SENSOR

(71) Applicant: Institut National de la Sante et de la Recherche Medicale (INSERM), Paris (FR)

(72) Inventors: Hugues De The, Paris (FR); Valerie Lallemand-Breitenbach, Paris (FR)

(73) Assignees: INSTITUT NATIONAL DE LA SANTE ET DE LA RECHERCHE MEDICALE (INSERM), Paris (FR); UNIVERSITE PARIS DIDEROT—PARIS 7, Paris (FR)

( * ) Notice: Subject to any disclaimer, the term of this patent is extended or adjusted under 35 U.S.C. 154(b) by 0 days.

(21) Appl. No.: 14/200,436

(22) Filed: Mar. 7, 2014

(65) Prior Publication Data
US 2014/0205568 A1    Jul. 24, 2014

Related U.S. Application Data

(62) Division of application No. 13/522,068, filed as application No. PCT/EP2011/050414 on Jan. 13, 2011, now Pat. No. 8,735,171.

(30) Foreign Application Priority Data

Jan. 13, 2010    (EP) .................................... 10305034

(51) Int. Cl.
| | |
|---|---|
| G01N 33/50 | (2006.01) |
| G01N 33/566 | (2006.01) |
| G01N 33/68 | (2006.01) |
| C07K 14/47 | (2006.01) |
| C07K 14/555 | (2006.01) |

(52) U.S. Cl.
CPC ............. *G01N 33/502* (2013.01); *C07K 14/47* (2013.01); *C07K 14/555* (2013.01); *G01N 33/5008* (2013.01); *G01N 33/6875* (2013.01)

(58) Field of Classification Search
None
See application file for complete search history.

(56) References Cited

FOREIGN PATENT DOCUMENTS

| EP | 1721615 | 11/2006 |
| WO | 2007/147892 | 12/2007 |
| WO | 2008/014619 | 2/2008 |

OTHER PUBLICATIONS

Barden et al., Pondering the Promyelocytic Leukemia Protein (PML) Puzzle: Possible Functions for PML Nuclear Bodies, Moll. Cell. Biol., 22, 5259-5269, 2002.
Dikshit et al. Role of ubiquitin protein ligases in the pathogenesis of polyglutamine diseases, Neurochem Res., 33, 945, 951, 2008.
Qin Q. et al.: "A novel GTPase: CRAG, mediates promyelocytic leukemia protein—associated nuclear body formation and degradation of expanded polyglutamine protein", J. Cell Biol., Feb. 13, 2006, pp. 407-504, vol. 172, No. 4.
Moran D.M. et al.: "Puromycin-based vectors promote a ROS-dependent recruitment of PML to nuclear inclusions enriched with HSP70 and Proteasomes", BMC Cell Biology, May 1, 2009, p. 32, vol. 10 No. 1, Biomed Central, London.
Chou W.-C. et al.: "Acute promyelocytic leukemia: recent advances in therapy and molecular basis of response to arsenic therapies", Curr. Opin. Hematol., Jan. 1, 2005, pp. 1-6, vol. 12, No. 1.
Nasr R. et al.: "Therapy-induced PML/RARA proteolysis and acute promyelocytic leukemia cure", Clin. Cancer Res., Oct. 15, 2009, pp. 6321-6326, vol. 15, No. 20.
Jeanne M. et al.: "PML/RARA Oxidation and Arsenic Binding Initiate the Antileukemia Response of As2O3", Cancer Cell, Jul. 13, 2010, pp. 88-98, vol. 18, No. 1.
Takahashi et al., PML nuclear bodies and neuronal intranuclear inclusion in polyglutamine diseases, Neurobiology of disease 13, 230-237, 2003.
Vigodner et al., Differential expression patterns of SUMO proteins in HL-60 cancer cell lines support a role for sumoylation in the development of drug resistance, Cell Tissue Res. 336, 277-286, 2009.
Blondel et al., Rabies virus P and small P products interact directly with PML and reorganize PMLnuclear bodies, Oncogene, 21, 7957-797, 2002.
Khelifi et al., Daxx is required for stress-induced cell death and JNK activation, Cell Death and Diff. 12, 724-733, 2005.

*Primary Examiner* — Elly-Gerald Stoica
(74) *Attorney, Agent, or Firm* — Whitham, Curtis, Christofferson & Cook, P.C.

(57) ABSTRACT

The present invention relates to a method for determining the redox status of a cell or tissue comprising a step consisting of determining the level of PML nuclear bodies in said cell or tissue.

3 Claims, No Drawings

DRUG MONITORING METHODS USING THE PROMYELOCYTIC LEUKEMIA PROTEIN AS A REDOX SENSOR

CROSS-REFERENCE TO RELATED APPLICATIONS

This application is a divisional of U.S. patent application Ser. No. 13/522,068 filed Oct. 1, 2012 and claims priority to the International Application No. PCT/EP2011/050414 filed Jan. 13, 2011 which claims priority to European Application 10305034.0 filed Jan. 13, 2010. The complete contents thereof are herein incorporated by reference.

FIELD OF THE INVENTION

The present invention relates to methods for determining the redox status of a cell or tissue. More particularly, the present invention relates to promyelocytic leukemia protein as a redox sensor.

BACKGROUND OF THE INVENTION

Many diseases associated with human aging, including cancer, cardiovascular disorders, and neurodegenerative diseases have a strong oxidative stress component, but the basic molecular mechanisms that connect aging, age-related diseases, and oxidative stress remain insufficiently understood.

Oxidative stress is the result of unregulated production of reactive oxygen species (ROS), and cellular mismanagement of oxidation-reduction chemistry can trigger subsequent oxidative damage to tissue and organs. In particular, hydrogen peroxide is a major ROS by-product in living organisms and a common marker for oxidative stress. The chemical biology of $H2O2$ is much more complex, however, as mounting evidence also supports a role for $H2O2$ as a second messenger in normal cellular signal transduction. Peroxide bursts in response to cell receptor stimulation can affect several classes of essential signaling proteins that control cell proliferation and/or cell death. Included are kinases like the mitogen-activated protein (MAP) kinase family, transcription factors such as nuclear factor [kappa]B (NF-[kappa]B), and activating protein 1 (AP-1) as well as various protein tyrosine phosphatases (PTPs), ion channels and G proteins. Despite the far-ranging consequences of $H2O2$ in human physiology and pathology, mechanistic details surrounding intracellular $H2O2$ generation, trafficking, and function remain elusive even in the simplest eukaryotic organisms.

Accordingly, interest in developing tools to study the physiological and pathological roles of $H2O2$ and related ROS in living systems is widespread. For example, fluorescent probes are well suited to meet the need for tools to map the spatial and temporal distribution of $H2O2$ within cells. Such reagents have revolutionized the study of calcium in biological systems and hold much promise for enhancing our understanding of $H2O2$ physiology and pathology. The major challenge for practical $H2O2$ sensing in biological environments is creating water-soluble systems that respond to $H2O2$ selectively over competing cellular ROS such as superoxide ($O2-$), nitric oxide (NO), and lipid peroxides. Several types of small-molecule reporters have been described for $H2O2$ detection. Included are dihydro derivatives of common fluorescent dyes (e.g., 2',7'-dichlorodihydrofluorescein, DCFH, and dihydrorhodamine 123, DHR), the Amplex Red/peroxidase system, phosphine-containing fluorophores, luminescent lanthanide complexes and chromophores with ROS-cleavable protecting groups. Limitations of these and other currently available responsive probes include interfering background fluorescence from competing ROS, potential side reactions with thiols that are present in high concentrations within cells, the need for external activating enzyme, lack of membrane permeability, and/or lack of water solubility or compatibility, requiring the use of organic co-solvents. Furthermore, these tools cannot be used on fixed or paraffin-embedded tissues, precluding their use in most pathological human situations, prospectively or retrospectively.

Therefore there is a need for new reliable redox sensor for determining the redox status of a cell.

SUMMARY OF THE INVENTION

The present invention relates to a method for determining the redox status of a cell or tissue comprising a step consisting of determining the level of promyelocytic leukemia protein (PML) nuclear bodies in said cell or tissue.

A further aspect of the invention relates to a method for determining the redox status of a cell or tissue comprising a step consisting of detecting the formation of disulfide-linked PML complexes, PML aggregation or formation of nuclear bodies in said cell or tissue.

DETAILED DESCRIPTION OF THE INVENTION

PML nuclear bodies (NBs) are matrix-associated domains that accumulate many sumoylated proteins. How NBs are assembled, what is their function and how $As2O3$ specifically triggers PML sumoylation remains unexplained. The inventors identify the redox potential as the critical determinant for NB formation. Upon oxidant stress or $As2O3$ exposure, PML forms disulfide-bond homodimers, which then multimerise in a matrix-associated NB outer shell. Thus, PML represents a redox sensor, whose oxidation regulates NB-formation. This property explains the action or arsenic in APL and pave the way for using PML to detect local changes in the redox status in vivo.

DEFINITIONS

Throughout the specification, several terms are employed and are defined in the following paragraphs.

As used herein, the term "Reactive Oxygen Species" (ROS) generally refers to radicals and other non-radical reactive oxygen intermediates that can participate in reactions giving rise to free radicals or that are damaging to organic substrates. Primary reactive oxygen species (ROS) such as superoxide radical, hydrogen peroxide, hydroxyl radicals, and ortho-quinone derivatives of catecholaranes exert their cellular effects by modifying DNA, lipids, and proteins to form secondary electrophiles. Examples of such latter secondary electrophiles include hydroxyalkenals, nucleotide propenals, and hydroxyperoxy fatty acyl chains. The secondary electrophiles are implicated in cellular dysfunction either because they are no longer able to participate in normal cellular activity or because they serve as electron acceptors in oxidative chain reactions that result in the modification of other essential cellular components. Damage caused by the primary and secondary ROS contributes to the etiology of human disease states caused by neuronal ischemia during stroke, post-cardiopulmonary bypass syndrome, brain trauma, and status epilepticus.

As used herein, the term "oxidative stress," generally refers to a physiological state of a cell or tissue characterized by the generation of ROS that exceeds the ability of said cell or tissue to at least partially neutralize or eliminate them. The imbalance can result from a lack of antioxidant capacity caused by disturbance in production, distribution, or by an overabundance of ROS.

As used herein, "redox state" and "redox status" are relative terms that generally refer to the presence and relative concentration of free radicals in a cell or tissue. Redox state influences oxidative stress experienced by a cell or tissue and accordingly organ. Changes in oxidative stress can influence the redox status of the cells.

As used herein, the term 'cell" refers to any eukaryotic cell. Eukaryotic cells include without limitation ovary cells, epithelial cells, circulating immune cells, cardiac cells, beta cells, hepatocytes, and neurons . . . .

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, the term "organ", when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

As used herein the term "Promyelocytic Leukemia protein" or "PML" is intended to include any molecule defined as such in the literature, comprising for example any types of PML and in particular, PML IV. The PML gene consist of nine exons and several alternative spliced PML transcripts have been described (de Thé et al., 1991; Fagioli et al., 1992; Goddard et al., 1991; Kakizuka et al., 1991; Kastner et al., 1992). PML belongs to a family of proteins defined by the presence of the RBCC motif, a C3HC4 (RING finger) zinc binding motif, one or two other cysteine-rich motifs, the B boxes and a coiled-coil region. PML is localised in the nuclear diffuse fraction of the nucleoplasm and in a discrete subnuclear compartment, the nuclear bodies (NBs) (Daniel et al., 1993; Dyck et al., 1994; Koken et al., 1994; Weis et al., 1994). The PML isoforms can be divided into seven groups, which we are designating as PML I-VII, on the basis of sequence differences, due to alternative splicing, at the C-terminus. It has been shown that PML III and PML IV exist without exon 5 (de Thé et al., 1991; Fagioli et al., 1992) and that PML V can exist without exons 5 and 6 or 4, 5 and 6 (Fagioli et al., 1992), although the sequences for the latter two isoforms are not available. Table 1 provides for the description of the PML isoforms with their corresponding accession numbers.

TABLE 1

Nomenclature for PML isoforms and alternative spliced variants

| Isoforms | | References | Accession |
|---|---|---|---|
| PML I | 882aa | PML4 (Fagioli et al., 1992) | |
| | 882aa | PML-1 (Goddard et al., 1991) | M79462 |
| | 882aa | TRIM19 alpha (Reymond et al., 2001) | AF230401 |
| PML II | 829aa | PML2 (Fagioli et al., 1992) | |
| | 824aa | PML-3 (Goddard et al., 1991) | M79464 |
| | 824aa | TRIM19 gamma (Reymond et al., 2001) | AF230403 |
| | 854aa | TRIM19 delta[1] (Reymond et al., 2001) | AF230404 |
| | 829aa | TRIM19 kappa (Reymond et al., 2001) | AF230410 |
| PML III | 641aa | PML-L (de The et al., 1991) | SS0913 |
| PML IIIa | 593aa | PML-S (de The et al., 1991) | |
| PML IV | 633aa | PML3 (Fagioli et al., 1992) | |
| | 633aa | Myl (Kastner et al., 1992) | X63131 |
| | 633aa | TRIM19 zeta (Reymond et al., 2001) | AF230406 |
| PML IVa | 585aa | TRIM19 lambda (Reymond et al., 2001) | AF230411 |
| PML V | 611aa | PML1 (Fagioli et al., 1992) | |
| | 611aa | PML-2 (Goddard et al., 1991) | M79463 |
| | 611aa | TRIM19 beta (Reymond et al., 2001) | AF230402 |
| PML VI | 560aa | PML-1 (Kakizuka et al., 1991) | M73778 |
| | 560aa | PML-3B (Goddard et al., 1991) | M80185 |
| | 560aa | TRIM19 epsilon (Reymond et al., 2001) | AF230405 |
| PML VIb | 423aa | TRIM19 iota[2] (Reymond et al., 2001) | AF230409 |
| PML VIb | 423aa | TRIM19 eta[2] (Reymond et al., 2001) | AF230407 |
| PML VIIb | 435aa | TRIM19 theta (Reymond et al., 2001) | AF230408 |

As used herein the term "PML nuclear bodies" or "NB" refers to donut-shaped nuclear domains containing PML protein (Hodges M, Tissot C, Howe K, Grimwade D, Freemont P S. Structure, organization, and dynamics of promyelocytic leukemia protein nuclear bodies. Am J Hum Genet. 1998; 63:297 304. doi: 10.1086.301991). PML nuclear bodies result from the aggregation of PML, notably by the formation of disulfide-linked PML complexes.

The term "subject" as used herein denotes a mammal such as a rodent, a feline, a canine and a primate. Preferably, a subject according to the invention is a human.

The term "healthy subjects" as used herein refers to a population of subjects who do not suffer from any known condition, and in particular, who are not affected with any disease that results from an oxidative stress.

The term "redox sensor", as used herein, refers generally to a protein the expression of which in a cell or tissue can be detected by standard methods in the art (as well as those disclosed herein), and is predictive or denotes redox status in said cell or tissue.

METHODS OF THE INVENTION

An aspect of the invention relates to a method for determining the redox status of a cell or tissue comprising a step consisting of determining the level of PML nuclear bodies in said cell or tissue.

A further aspect of the invention relates to a method for determining the redox status of a cell or tissue comprising a step consisting of detecting the formation of disulfide-linked PML complexes, PML aggregation or formation of nuclear bodies in said cell or tissue.

Determination of level of PML nuclear bodies or detection of the formation of disulfide-linked PML complexes, PML aggregation or formation of nuclear bodies may be performed by a variety of techniques. Generally, the methods involve contacting the cell with a binding partner capable of selectively interacting with PML. The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique.

Alternatively, techniques described for the production of single chain antibodies (see e.g. U.S. Pat. No. 4,946,778) can be adapted to produce anti-PML, single chain antibodies. Antibodies useful in practicing the present invention also include anti-PML fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to PML. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Monoclonal antibodies for PML are described in the prior art. For example PGM3 is a commercially available antibody directed towards the N-terminus of the protein. Another example includes C7 antibody that is commercially available from ABCAM.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S.D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the binding of the binding partner (ie. Antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The level of PML nuclear bodies (or detection of the formation of disulfide-linked PML complexes, PML aggregation or formation of nuclear bodies) may be determined by any well known techniques in the art.

For example an immunohistochemistry (IHC) method may be used. IHC specifically provides a method of detecting targets in a sample or tissue specimen in situ. The overall cellular integrity of the sample is maintained in IHC, thus allowing detection of both the presence and location of the targets of interest. Typically a sample is fixed with formalin, embedded in paraffin and cut into sections for staining and subsequent inspection by light microscopy. Frozen samples may also be used. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirci Corp, Tokyo, Japan). In particular embodiment, a tissue section may be mounted on a slide or other support after incubation with antibodies directed against the proteins encoded by the genes of interest. Then, microscopic inspections in the sample mounted on a suitable solid support may be performed. For the production of photomicrographs, sections comprising samples may be mounted on a glass slide or other planar support, to highlight by selective staining the presence of the proteins of interest. Therefore IHC samples may include, for instance: (a) preparations comprising cumulus cells (b) fixed and embedded said cells and (c) detecting the proteins of interest in said cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

Another method includes immunofluorescence. Immunofluorescence is a technique allowing the visualization of a specific protein in cells or tissue sections by binding a specific antibody chemically conjugated with a fluorescent dye such as fluorescein isothiocyanate (FITC). There are two major types of immunofluorescence staining methods: 1) direct immunofluorescence staining in which the primary antibody is labeled with fluorescence dye, and 2) indirect immunofluorescence staining in which a secondary antibody labeled with fluorochrome is used to recognize a primary antibody. Immunofluorescence staining can be performed on cells fixed on slides and tissue sections. Immunofluorescence stained samples are examined under a fluorescence microscope or confocal microscope. Typically, primary, or direct, immunofluorescence uses a single antibody that is chemically linked to a fluorophore. The antibody recognises the target molecule and binds to it, and the fluorophore it carries can be detected via microscope. This technique has several advantages over the secondary (or indirect) protocol below because of the direct conjugation of the antibody to the fluorophore. This reduces the number of steps in the staining procedure, is therefore faster, and can avoid some issues with antibody cross-reactivity or non-specificity, which can lead to increased background signal.

In one embodiment, the method of the invention further may comprise a step of comparing the level of PML nuclear bodies (or detection of the formation of disulfide-linked PML complexes, PML aggregation or formation of nuclear bodies) in the cell or tissue with a predetermined threshold value. Said comparison is indicative of the redox status in said cell or tissue. For example, the predetermined value may the level of PML nuclear bodies determined in a cell or tissue which does not undergo an oxidative stress. Therefore, the predetermined value may the level of PML nuclear bodies in a cell or tissue isolated from a healthy subject. In this case a higher level of PML nuclear bodies in the cell or tissue compared to the predetermined value is indicative of that the cell or tissue undergoes an oxidative stress.

Biochemical methods may also be useful especially for detecting the formation of disulfide-linked PML complexes. Typically immunoblotting assay under non-reducing conditions as described in Example 1 may be suitable.

The method of the invention is particularly suitable for determining the redox status of a whole subject, by determining step of determining the redox status of at least one cell or tissue sample obtained from said subject. In a preferred embodiment, said method involves using several cell or tissue samples obtained from the subject.

The sample can be a biological fluid such as whole blood, plasma, serum, nasal secretions, sputum, saliva, urine, sweat, transdermal exudates, cerebrospinal fluid, or the like. Alternatively, sources of such samples include muscle, eye, skin, gonads, lymph nodes, heart, brain, lung, liver, kidney, spleen, thymus, pancreas, solid tumors, macrophages, mammary glands, mesothelium, and the like. Cell samples include without limitation ovary cells, epithelial cells, circulating immune cells, .beta cells, hepatocytes, and neurons.

The method of the invention is also particularly suitable to determine whether a subject has or is predisposed to having a disease characterized by a strong oxidative stress component. Actually, if not regulated properly, the excess ROS can damage the lipids, protein or DNA of a cell, altering its normal function and leading ultimately to the development of certain disease states. The etiology of diseases involving oxidative stress is in part related to the damage caused by the primary and secondary ROS. ROS contribute to the pathogenesis of important human diseases caused by neuronal ischemia during stroke, post-cardiopulmonary bypass syndrome, brain trauma, and status epilepticus. ROS are also involved in cardiac damage induced during ischemic heart disease, renal damage induced by ischemia and toxins as well as in more chronic diseases such as the destruction of neurons in Parkinson's disease, Amyloidosis, Prion disorders, Alzheimer's disease, and other chronic neurodegenerative disorders. Autoimmune diseases such as the destruction of the islets of Langerhans of the endocrine pancreas in Diabetes Mellitus are also encompassed.

Accordingly a further aspect of the invention relates to a method of testing a subject thought to have or be predisposed to having a disease characterized by a strong oxidative stress component comprising the step of determining the redox status a cell or tissue sample obtained from said subject.

The method of the invention is also particularly suitable for determining the impact of a compound on the redox status of a cell or tissue. Therefore according to one embodiment the invention relates to a method for determining the impact of a compound on the redox status of a cell or tissue comprising the steps consisting of:

i) determining the redox status of a cell or tissue by performing the method as above described ii) contacting said cell or tissue with said compound iii) determining the redox status of said cell or tissue after step ii) by performing the method as above described iv) and comparing the redox status determined at step iii) with the redox status determined a step i).

In a particular embodiment, the cell at step ii) may be genetically transformed with at least one nucleic acid molecule encoding for PML. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acid molecule may also include a fusion partner so that the recombinant polypeptide is expressed as a fusion polypeptide consisting of PML fused to said fusion partner. The main advantages of fusion partners are that they assist detection of said fusion polypeptide and also enhance protein expression levels and overall yield. Typically, the fusion partner is green fluorescent protein (GFP). This fusion partner serves as a fluorescent "tag" which allows the fusion polypeptide of the invention to be detected by fluorescence microscopy. The GFP tag is useful when assessing subcellular localization of the fusion polypeptide of the invention.

Typically, said transformation may be performed by using any vector well known in the art. Examples of suitable vectors include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, Psi-CRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

According to one embodiment, the compound may be natural or not. Accordingly, the compound may be selected from the group consisting of chemical entities (e.g. a small organic molecule) or biological entities (such as protein, nucleic acid).

Actually, said method may be particularly suitable for toxicological assays, to determine the toxicological effect of a material (e.g., plastic) or a drug.

The method may be also particularly suitable for screening drugs useful for reducing oxidative stress.

Therefore according to one embodiment, the present invention relates to a method for screening a drug for reducing oxidative stress comprising the steps consisting of:
i) providing a candidate compound
ii) contacting a cell or tissue with said candidate compound
iii) determining the level of PML nuclear bodies in said cell or tissue
iv) comparing the level of PML nuclear bodies measured at step iii) with a predetermined value
v) and selecting the candidate compound which induce a lower level of PML nuclear bodies than the predetermined value.

The candidate compound may be of various origin, nature and composition. It may be any organic or inorganic substance, such as a lipid, peptide, polypeptide, nucleic acid, small molecule, etc., in isolated or in mixture with other substances. The compounds may be all or part of a combinatorial library of products, for instance.

According to one embodiment, the cell or tissue at step ii) may be isolated from a subject having a disease characterized by a strong oxidative stress component. In another embodiment, the cell or tissue may be contacted with an agent known for inducing stress before, after or simultaneously with the candidate compound. For example, said agent may be H2O2, Paraquat or As2O3.

Alternatively, the cell at step ii) may be genetically transformed with at least one nucleic acid molecule encoding for PML or a fusion polypeptide as above described.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

The candidate compound may be also compared with a compound well known in the art for reducing oxidative stress such as an antioxidant.

The candidate compounds that have been positively selected at the end of step v) may be then subjected to further selection steps in view of further assaying its in vivo properties. For example, the candidate compound may be administered in animal models for a disease characterized by a strong oxidative stress component.

The method of the invention is also particularly suitable for monitoring the redox status of a cell or tissue at different time intervals.

The present invention is also particularly suitable for monitoring a treatment of a subject with a drug for reducing oxidative stress comprising determining the redox status of a cell or tissue sample obtained from the subject by performing the method of the invention, and optionally, comparing said redox status with a predetermined value representing a predetermined stage of oxidative stress, the redox status of said cell or tissue with respect to the predetermined value indicating the evolution of the oxidative stress in said patient, and therefore the degree of efficacy of the treatment.

A further aspect of the invention relates to PML a redox sensor.

A further aspect of the invention relates to PML for use in the treatment of a disease characterized by a strong oxidative stress component.

Said diseases include but are not limited to cancer, diseases caused by neuronal ischemia during stroke, post-cardiopulmonary bypass syndrome, brain trauma, and status epilepticus, cardiac damage induced during ischemic heart disease, renal damage induced by ischemia and toxins as well as in more chronic diseases such as the destruction of neurons in Parkinson's disease, Amyloidosis, Prion disorders, Alzheimer's disease, and other chronic neurodegenerative disorders. Autoimmune diseases such as the destruction of the islets of Langerhans of the endocrine pancreas in Diabetes Mellitus are also encompassed.

Indeed without wishing to be bound by any theory, the inventors believe that PML represents a tampon for reactive oxygen species and thus may eventually contribute to the control of the redox status of the cell tissue or organ.

According to the invention it should be understood that those of skill in the art may use any protein or gene sequence variant as long as it has the properties of PML. "Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

In specific embodiments, it is contemplated that PML polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

According to the invention, PML polypeptides may be produced by conventional automated peptide synthesis methods or by recombinant expression. General principles for designing and making proteins are well known to those of skill in the art.

Another aspect of the invention relates to a nucleic acid molecule encoding for PML for use in the treatment of a disease characterized by a strong oxidative stress component.

Typically, said nucleic acid is a DNA or RNA molecule, which may be included in any suitable vector, such as a plasmid, cosmid, episome, artificial chromosome, phage or a viral vector as above described.

So, a further object of the invention relates to a vector comprising a nucleic acid encoding for PML for use in the treatment of a disease characterized by a strong oxidative stress component.

A further object of the invention relates to a host cell comprising a nucleic acid encoding for PML (or a vector comprising a nucleic acid thereof) for use in the treatment of a disease characterized by a strong oxidative stress component.

Alternatively, it may be particularly suitable to use an inducer of PML expression for treating a disease characterized by a strong oxidative stress.

As use herein, the term "inducer of Promyelocytic Leukemia protein (PML) expression" denotes a compound, natural or not, which has the capability to up regulate or activate the expression of a gene encoding for PML and consequently the expression of the corresponding protein.

Accordingly, a further aspect of the invention relates to an inducer of PML expression for use in the treatment of a disease characterized by a strong oxidative component.

In a particular embodiment, the inducer of PML expression is selected from the group consisting of interferons, including all types of interferons such as alpha, beta, omega and gamma intereferons. In a preferred embodiment the inducer of PML expression includes interferon-alpha.

An "interferon" or "IFN", as used herein, is intended to include any molecule defined as such in the literature, comprising for example any types of IFNs (type I and type II) and in particular, IFN-alpha, IFN-beta, INF-omega and IFN-gamma. The term interferon, as used herein, is also intended to encompass salts, functional derivatives, variants, muteins, fused proteins, analogs and active fragments thereof. The polypeptide sequences for human interferon-alpha are deposited in database under accession numbers: AAA 52716, AAA 52724, and AAA 52713. The polypeptide sequences for human interferon-beta are deposited in database under accession numbers AAC41702, NP_002167, AAH 96152, AAH 96153, AAH 96150, AAH 96151, AAH 69314, and AAH 36040. The polypeptide sequences for human interferon-gamma are deposited in database under accession numbers AAB 59534, AAM 28885, CAA 44325, AAK 95388, CAA 00226, AAP 20100, AAP 20098, AAK 53058, and NP-000610.

In a preferred embodiment the interferon is interferon-alpha. Interferon-alpha includes, but is not limited to, recombinant interferon-α2a (such as ROFERON® interferon available from Hoffman-LaRoche, Nutley, N.J.), interferon-α2b (such as Intron-A interferon available from Schering Corp., Kenilworth, N.J., USA), a consensus interferon, and a purified interferon-α product.

According to the invention, the compounds as above described (PML, nucleic acid vectors, inducer of PML expression) may be formulated as pharmaceutical compositions. The pharmaceutical composition according to the invention may further comprise a pharmaceutically carrier or excipient. The term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The compounds may be combined with pharmaceutically acceptable excipients, and optionally sustained-release matrices, such as biodegradable polymers, to form therapeutic compositions. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder, activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

A further aspect of the invention relates to a method of testing a patient thought to be predisposed to a disease characterized by a strong oxidative component, which comprises the step of analyzing a sample from said patient for detecting the presence of a mutation in the gene encoding for PML and/or its associated promoter.

Typically, the sample may a blood sample.

Typical techniques for detecting a mutation in the gene encoding for PML may include restriction fragment length polymorphism, hybridisation techniques, DNA sequencing, exonuclease resistance, microsequencing, solid phase extension using ddNTPs, extension in solution using ddNTPs, oligonucleotide assays, methods for detecting single nucleotide polymorphism such as dynamic allele-specific hybridisation, ligation chain reaction, mini-sequencing, DNA "chips", allele-specific oligonucleotide hybridisation with single or dual-labelled probes merged with PCR or with molecular beacons, and others.

The invention will be further illustrated by the following figures and examples. However, these examples and figures should not be interpreted in any way as limiting the scope of the present invention.

Example 1

Material & Methods

Constructs and SiRNAs

PMLΔSIM, PML 3K/RΔSIM mutants and GFP-SIM were constructed by deletion or insertion of the PML SIM coding sequence (amino acids 556 to 566) with the Quickchange II site-mutagenesis kit (Qiagen) into pSG5-PML, pSG5-PML 3K/R, or pEGFP-N1. Expression vectors for PML PML, 3K/R and C60A mutants were described previously[15] and PMLC212A, PML B1 (C140/143/148A) were also constructed by mutagenesis on pSG5-PML or MSCV-PML. PMLΔCC corresponds to the deletion of the coiled coil motif (amino acids 216 to 333). Unless otherwise indicated, PML refers to the PML-III isoform. PML and Sp100 were fused with MBP in the pMalC2 vector. SUMO-1, 2 and 3 cDNA, deleted from the 5' diglycine coding sequence, were amplified by PCR and cloned in the BglII/HindIII restriction sites of pEGFP-N1. Fusions of the Daxx or Hipk2 SIM (amino acids 730 to 741 and 857 to 871 respectively) to GFP (pEGFP-C1-SIM$_{Daxx\ or\ HipK2}$), and deletion from the pSG5-Daxx were similarly constructed. TDG sumoylation site (amino acids 325 to 335)[36] was inserted in pEGFP-SIM$_{(PML)}$ by mutagenesis. PML-III was cloned in pECFP-C1 and SUMO-1 in pEYFP-C1; fusions were then sub-cloned in the MSCV vector. SiRNAs against SUMO-s were described previously[25].

Cell Lines, Transfections and Treatments

HeLa, MRC5, CHO, COS, SaOS and Pml−/− MEF cells were cultured in 10% Fetal calf serum DMEM medium (Gibco). Plasmid transfections were performed in CHO or COS with Effectene transfection reagent (Qiagen). Stable CHO cell lines, expressing the PML isoform, or its mutants, were obtained by cotransfection of pSG5-PMLΔSIM, pSG5-3K/RΔSIM, pSG5-C212A or pSG5-B1 with the Dsp-Hygro vector; selected for 2 weeks in 800 mg/ml hygromycin-containing media. Clones were selected for similar PML expression levels. PML WT, PML C60A, PMLΔCC and PML 3K/R stable expressing cell lines were described previously[25]. MRC5 or SaOS were grown on coverslips and treated with 400 U/ml IFNg for 48 h and IFNa for 24 h to induce PML expression. Primary mouse APL blasts were obtained from serially transplanted APLs[16] and then cultured in RPMI medium, 10% FCS supplemented with IL-3, IL-6 and SCF (Gibco). Infection of immortalized pml−/− MEFs or primary progenitors was performed with retroviruses produced by CaCl$_2$ transfection of Plat-E cells by with the MSCV-PML/RARA retroviral vector[16]. Pml−/− or +/+ MEF cells were similarly transduced with MSCV-PML or PML mutants.

As$_2$O$_3$ (Fluka) treatments were performed at 1 mM or 10 mM for 1 h. H$_2$O$_2$ from SIGMA-Aldrich was performed for 30 min at 0.1, 1 or 10 mM as indicated, Phenylarsine oxide (PAO) was purchased from SIGMA, solubilized at 50 mg/ml in DMSO and used at 0.1 mM, 1 mM or 10 mM for 1 h, CdCl$_2$ from Flucka, was used at a final concentration of 10 mM. Cells were treated with 10 mM Lactacystin (Calbiochem) overnight, and with 50 mg/ml ready-made cycloheximide (SIGMA) as indicated. Pre-treatments with 100 mM N-ethyl maleimide (NEM) (SIGMA) for 30 min were carried out before adding As$_2$O$_3$ or H$_2$O$_2$. TC-FlAsH (FlAs) was from Molecular Probes; cells growing on coverslips were treated with 1 mM for 1 h, washed in PBS before PFA fixation. Dithiarsolan-biotin conjugate (arsenic-biotin) was kindly given by Kenneth L. Kirk[53], solubilized in DMSO to a 5 mM stock solution, and used on cell culture at 10 mM for 1 h.

Protein Analysis

Cell lysates were resolved on 7%, 3 to 10% gradient or 12% SDS-PAGE gels and transferred onto nitrocellulose membranes. Detection was performed with the chemi-luminescent substrate SuperSignal WestPico (Pearce), using previously described home made mouse and chicken anti-hPML antibodies[15,25], the PML isoform-specific antibodies were characterized previously[29]. For analysis under non-reducing conditions, b-Mercapto-Ethanol or DTT was omitted from the standard Laemmli buffer. In situ nuclear matrix was prepared as for immunofluorescence, but finally resuspended in Laemmli buffer. Purifications of 6M Guanidium-HCl denatured (His×6)-tagged proteins were done with Ni-NTA-agarose from Qiagen, as previously[25]. The purification of the arsenic-bound proteins were performed from As-biotin treated CHO-PML or transiently pSG5-PML wt or C212A transfected COS cells. Cells were lysed in 2% SDS-containing RIPA with Protease Inhibitor Cocktail (PIC) (Roche Applied Science), denatured at 95° C. for 5 min to release nuclear matrix-associated PML. Streptavidin-agarose (Molecular Probes) was added to the 03% SDS lysates for 30 min to 1 h, washed three times in RIPA and arsenic bound proteins were eluted in Laemmli buffer.

Microscopy and Antibodies

Immunofluorescence, electronic microscopy and antibodies were previously described[15]. In situ nuclear matrix preparations were prepared as described[1]. Confocal analyses were performed on a LSM510 Meta laser microscope (Carl Zeiss MicroImaging, Inc.) with a plan apochromat 63X N.A.1.4 oil immersion objective and increased resolution images were obtained with deconvolution software (Autodeblur, Image Quant) using blind iterative algorithms.

The mouse anti-GFP antibody was from Roche Applied Science; Goat polyclonal anti-Lamin B (M20), rabbit polyclonal anti-RXRa (D20) and anti-Daxx (M-112) were from Santa Cruz Biotechnology. Rabbit polyclonal anti-Daxx from G. Grosveld was used for Western blot analysis. Anti SUMO-1 (mouse monoclonal anti GMP-1 antibody) and Rabbit polyclonal anti-SUMO-2/3 antibodies were from Zymed Laboratories. Rabbit polyclonal anti-RARA115 was a kind gift of Pierre Chambon. All the antibodies were revealed by AlexaFluor 488 or 594-labeled secondary antibodies from Molecular Probes. Fluorescence was quantified with ImageJ software.

Fluorescence Recovery after Photobleaching

FRAP experiments were carried out on a LSM510 Meta confocal microscope. For recovery of CFP-PML and YFP-SUMO-1 in MEFs, 4 images before and 60 after bleach were taken, with 10 sec between acquisitions. Bleach pulses were performed 6 times in ROI containing one NB, with maximum laser intensities. Pinhole was adjusted to 1 and optimal laser power was adjusted to minimize bleaching during recovery. For As$_2$O$_3$ treated cells, FRAP was assessed 8 min, 20 min, 30 min and 1 h after drug addition. For SUMOΔGG-GFP and GFP-SIM fusions, FRAP was performed at zoom 20, maximum speed scan (0.05 sec between acquisitions), 10 images were acquired before bleach, 3 iterations were used to bleach, and time of recovery was between 15 and 30 sec.

Animal Experiments

Mouse experiments were repeated 3 times. Animal handling was done according to the guidelines of institutional animal care committees, using protocols approved by "Comité Régional d'Ethique Expérimentation Animale (CREEA) no 4". 25 mg/kg Paraquat (SIGMA) was daily intraperitoneally injected in PML/RARA and PML/RARA-S77A leukemic mice[17] (to be fully described elsewhere). In vivo imaging was performed using a Xenogen IVIS100 facility to ensure similar tumor mass pre-treatment. Mice were treated with 150 mg/kg for 1 h before bone marrow cytospins (from FVB/NICO) and 0.5 mm tumor cryosections (NUDE/SWISS) immuno-histochemistry; CHO-PML xenografts were performed as before[42].

Statistics

The two-sided t-test was performed to validate the significance of the observed differences, which were considered statistically significant when P<0.05

Example 2

PML Nuclear Bodies Biogenesis Involves PML Oxidation

Intermolecular disulfide bonds were previously implicated in stabilization of the nuclear matrix. Interestingly, upon exposure to DTT (a di-thiol reductant), PML NB labelling was lost from in situ matrix preparations, while lamin B staining was unaffected, suggesting that disulfide bonds tether PML onto the nuclear matrix. In PML transfected cells, Western-blot analysis under non-reducing conditions revealed high molecular weight species that disappeared in reducing conditions, suggesting the existence of disulfide-linked PML complexes. To demonstrate that these complexes are covalent PML dimers, we transiently co-expressed (His)×6-PML-V with a CFP-PML-III fusion and analysed the lysates by Western-blot in non-reducing conditions with isoform-specific antibodies. A specific complex of the expected antibody reactivity for PML-III/PML-V heterodimers was observed, formally demonstrating that PML forms disulfide-bond dimers. We then compared total and nuclear matrix extracts from transiently transfected CHO cells under non-reducing conditions and observed that the matrix fraction was dramatically enriched in covalent PML dimers. Similar results were obtained with PMLΔSIM, PML3KR or PML3KRΔSIM, again demonstrating that matrix-association is independent of PML SUMO/SIM interactions, but is associated with PML oxidation.

Disulfide bonds are oxidant-sensitive. We thus treated transiently PML- or PML3KR-transfected cells with the ROS-inducers As2O3 or H2O2 and observed a dramatic increase in covalent PML homodimers. As expected, the thiol alkylator N-ethyl-maleimine (NEM) abrogated As2O3 or H2O2-enhanced homodimer formation, but also disrupted PML NBs in untreated cells. As ROS status is profoundly altered in cell culture, we examined NBs in vivo in basal conditions and after acute induction of ROS. While prominent NBs were observed in CHO-PML cells grown in culture, NBs were undetectable when these same cells were grown as xenografts in nude mice under physiological oxygen conditions. However, a dramatic increase in NBs was observed when mice were treated with Paraquat, which induces ROS formation. Identical results were obtained with endogenous murine pml in normal bone marrow cells. Thus, oxidation-triggered disulfide bonds in PML regulate its partitioning between the nucleoplasm and nuclear matrix associated NBs.

These experiments identify ROS as the key regulator of nucleoplasmic/NB partitioning and NB biogenesis. Conversely, in amino acid-starved cultures, acquired NB-defects were only corrected by cysteine, suggesting that intracellular —SH content exerts some control over NB-morphogenesis40. Most cell-lines show abundant NBs, likely reflecting the high oxygen tension in culture. Absence of NBs in most normal cells and tissues in vivo and their prominence in cells exposed to ROS, such as monocytes, granulocytes or undergoing apoptosis, inflammation or early transformation, are fully consistent with ROS being critical regulators of NB-aggregation in vivo. Thus, PML could be a ROS sensor and NBs, biomarkers of redox status in vivo.

Example 3

Matrix-Associated PML is Oxidized

The matrix-associated PML fraction is hypersumoylated. Conversely, deletion of the coiled-coil of PML abrogates its association to the nuclear matrix, NB formation, and sumoylation. Thus, whereas As2O3 induces PML targeting to the matrix and NB formation independently of sumoylation, matrix association contributes to basal or As2O3-enhanced PML sumoylation. We therefore questioned how As2O3 could promote transfer from soluble diffuse nuclear PML to insoluble, matrix-associated NBs. As2O3 controls protein phosphorylation and ROS production. We could not confirm in our experimental system that As2O3-induced PML phosphorylation by ERK1/2 controls PML sumoylation. We then examined whether As2O3-induced ROS could promote NB formation through PML disulfide formation, as intermolecular disulfide bonds were implicated in stabilizing the nuclear matrix. We observed that treatment with DTT (a dithiol reductant) of nuclear matrix prepared in situ disrupted endogenous PML NBs, without affecting lamin-B staining. Similarly, a 1 hr treatment of CHO cells stably expressing the PML-III isoform (CHO-PML) with the thiol alkylator N-ethylmaleimide (NEM) disrupted basal PML NBs. Finally, most CHO-PML cells cultured for 10 days in the presence of the ROS scavenger N-acetyl cysteine (NAC) lost basal NB formation. NBs were restored by a 3 day wash-out. Thus, cysteine residues and ROS regulate NB biogenesis.

NBs are matrix-associated domains. When analyzed in the absence of reducing agents (DTT or βME), the nuclear matrix fraction of transiently PML-transfected CHO cells entirely consisted of high molecular weight PML species. DTT disrupts disulfide bridges and may also reduce SOH or SOS linkages. The observation that these high molecular weight PML complexes reversed to monomeric species upon reduction, strongly suggested that matrix-associated PML consists of intermolecularly disulfide-bound PML multimers. Accordingly, pretreatment of CHO cells with NAC prior to PML transfection led to a dramatic decrease in the abundance of the high molecular weight PML forms. To formally demonstrate the existence of covalent PML multimers, we transiently expressed (His)×6-PML-V with or without CFP-PML-III (PML isoforms of different sizes) in the presence of As2O3. Denatured whole-cell lysates were analyzed under nonreducing conditions with isoform-specific antibodies. In cotransfected cells only, several, rather than one, high molecular weight complexes were detected with the PML-V-specific antibody. Only the highest species reacted with anti-PML-III, implying that these were PML-III/PML-V multimers. PML-multimerization was also demonstrated by immunoprecipitating SDS-denatured lysates with anti-PML-III-specific sera, followed by guanidinium denaturation and His-purification of the (His)×6-PML-V-containing complexes. Under nonreducing conditions, only cells expressing both PML isoforms yielded high molecular weight PML-III- and PML-V-reactive conjugates, which shifted to the monomeric state after reduction. Finally, mass spectrometric analysis of high molecular weight PML complexes purified under denaturing conditions from As2O3-treated cells consisted primarily of PML peptides (54%). Other detected proteins are most likely contaminants, given that the most abundant one represented <6% of the total peptides. Collectively, these analyses strongly argue against heterodimer formation with a distinct protein. Thus, although we cannot rule out the existence of intramolecular disulfide linkages, these data indicate that intermolecular PML crosslinking by ROS-induced disulfides is associated with its presence in the nuclear matrix and with NB-formation.

We next investigated whether oxidants enhance disulfide-bound PML multimerization. A short exposure to therapeutic levels of As2O3 (or to other oxidants, such as H2O2 or CdCl2, massively increased the amounts of covalent PML multimers in CHO cells transiently overexpressing PML. In stable CHO transfectants, oxidants similarly induced PML multimerization, whereas arsenical also promoted PML sumoylation. Formation of covalent multimers in transiently PML-transfected CHO cells was abrogated by pretreatment with NEM or NAC. If PML covalent multimerization by ROS is indeed the primary event initiating As2O3 effects, other oxidants should mimic As2O3-enhanced NB biogenesis. Yet, strong oxidants ($CdCl_2$, $H_2O_2$) disrupt NBs in cultured cells, possibly because these agents fully oxidize some critical cysteines into cysteic acid, precluding disulfide formation and thus dissociating NBs. We thus examined whether paraquat, an acute ROS inducer, would regulate NB formation in vivo, a setting where ROS levels are likely more controlled. Although CHO-PML cells grown ex vivo displayed prominent NBs, those were barely detectable when these cells were grown as xenografts in nude mice. This could suggest that the microenvironment (notably oxygen tension) in vivo does not favor NB formation, whereas ex vivo culture under hyperoxic conditions evokes NB aggregation. Critically, paraquat or As2O3 treatment of mice bearing CHO-PML xenografts elicited a dramatic increase in NB formation (containing both PML and its partner daxx). Western blot analysis under non-reducing conditions showed the occurrence of PML multimers in CHO-PML xenografts derived from oxidant-treated mice. Enhanced NB formation by endogenous murine PML was also observed in bone marrow cells on treatment with paraquat or As2O3 treatment. Altogether, these data demonstrate that, in vivo, ROS inducers mimic As2O3 as to the regulation of PML oxidation, NB formation, and partner recruitment.

We first demonstrate that ROS regulate NB-biogenesis in vivo, explaining the abundance of NBs in multiple stress conditions or in cells exposed to high oxygen concentrations, such as endothelial cells ([Koken et al., 1995] and [Lallemand-Breitenbach and de Thé, 2010]). NBs are nuclear matrix domains and disulfides were previously implicated in nuclear matrix formation ([Kaufmann et al., 1991] and [Stuurman et al., 1992b]). PML is the first example of a protein organizing a nuclear domain in a ROS-dependent manner, suggesting that PML is a ROS sensor. Both ROS and PML have been implicated in multiple biological processes, notably DNA damage response, senescence, and stem cell self-renewal, as well as in the fine-tuning of some critical signaling pathways, including HIF1a or PTEN/AKT ([Song et al., 2008], [Trotman et al., 2006], [Bernardi and Pandolfi, 2007], [Ito et al., 2008] and [Pearson et al., 2000]). PML NB formation could thus mediate some effects of basal ROS. In cellulose synthase, cysteines arranged in a zinc finger become engaged into multiple intermolecular disulfides upon ROS exposure (Kurek et al., 2002). This ROS-induced, oxidation-mediated, transition is responsible for the action of herbicides on cellulose synthase activity. PML, which harbors three zinc fingers, forms several disulfide bridges, likely all required for full matrix association and PML sumoylation. This could explain why, despite formation of some disulfide bridges, the C212A mutant exhibits a defective sumoylation. Matrix association and/or sumoylation might also require an interchain zinc finger (Callaghan et al., 2005), itself possibly involving C212.

REFERENCES

Throughout this application, various references describe the state of the art to which this invention pertains. The disclosures of these references are hereby incorporated by reference into the present disclosure.

Bernardi and Pandolfi, 2007 R. Bernardi and P. P. Pandolfi, Structure, dynamics and functions of promyelocytic leukaemia nuclear bodies, Nat. Rev. Mol. Cell Biol. 8 (2007), pp. 1006-1016.

Callaghan et al., 2005 A. J. Callaghan, Y. Redko, L. M. Murphy, J. G. Grossmann, D. Yates, E. Garman, L. L. Ilag, C. V. Robinson, M. F. Symmons, K. J. McDowall and B. F. Luisi, "Zn-link": A metal-sharing interface that organizes the quaternary structure and catalytic site of the endoribonuclease, RNase E, Biochemistry 44 (2005), pp. 4667-4675.

Ito et al., 2008 K. Ito, R. Bernardi, A. Morotti, S. Matsuoka, G. Saglio, Y. Ikeda, J. Rosenblatt, D. E. Avigan, J. Teruya-Feldstein and P. P. Pandolfi, PML targeting eradicates quiescent leukaemia-initiating cells, Nature 453 (2008), pp. 1072-1078.

Kaufmann et al., 1991 S. H. Kaufmann, G. Brunet, B. Talbot, D. Lamarr, C. Dumas, J. H. Shaper and G. Poirier, Association of poly(ADP-ribose) polymerase with the nuclear matrix: The role of intermolecular disulfide bond formation, RNA retention, and cell type, Exp. Cell Res. 192 (1991), pp. 524-535.

Koken et al., 1995 M. H. M. Koken, G. Linares-Cruz, F. Quignon, A. Viron, M. K. Chelbi-Alix, J. Sobczak-Thépot, L. Juhlin, L. Degos, F. Calvo and H. de Thé, The PML growth-suppressor has an altered expression in human oncogenesis, Oncogene 10 (1995), pp. 1315-1324. View Record in Scopus I Cited By in Scopus (190)

Kurek et al., 2002 I. Kurek, Y. Kawagoe, D. Jacob-Wilk, M. Doblin and D. Delmer, Dimerization of cotton fiber cellulose synthase catalytic subunits occurs via oxidation of the zinc-binding domains, Proc. Natl. Acad. Sci. USA 99 (2002), pp. 11109-11114.

Lallemand-Breitenbach and de Thé, 2010 V. Lallemand-Breitenbach and H. de Thé, PML nuclear bodies, Cold Spring Harb. Perspect. Biol. 2 (2010), p. a000661.

Pearson et al., 2000 M. Pearson, R. Carbone, C. Sebastiani, M. Cioce, M. Fagioli, S. Saito, Y. Higashimoto, E. Appella, S. Minucci, P. P. Pandolfi and P. G. Pelicci, PML regulates p53 acetylation and premature senescence induced by oncogenic Ras, Nature 406 (2000), pp. 207 210.

Song et al., 2008 M. S. Song, L. Salmena, A. Carracedo, A. Egia, F. Lo-Coco, J. Teruya-Feldstein and P. P. Pandolfi, The deubiquitinylation and localization of PTEN are regulated by a HAUSP-PML network, Nature 455 (2008), pp. 813-817.

Stuurman et al., 1992b N. Stuurman, A. Floore, A. Colen, L. de Jong and R. van Driel, Stabilization of the nuclear matrix by disulfide bridges: Identification of matrix polypeptides that form disulfides, Exp. Cell Res. 200 (1992), pp. 285-294. Article|PDF (3013 K)|View Record in Scopus|Cited By in Scopus (23)

Trotman et al., 2006 L. C. Trotman, A. Alimonti, P. P. Scaglioni, J. A. Koutcher, C. Cordon-Cardo and P. P. Pandolfi, Identification of a tumour suppressor network opposing nuclear Akt function, Nature 441 (2006), pp. 523-527.

The invention claimed is:

1. A method for determining the impact of a compound on the redox status of a cell or tissue comprising the steps of:
   i) determining the redox status of a cell or tissue by detecting the formation of disulfide-linked promyelocytic leukemia protein (PML) complexes in said cell or tissue
   ii) contacting said cell or tissue with said compound
   iii) determining the redox status of said cell or tissue after step ii) by detecting the formation of disulfide-linked PML complexes in said cell or tissue; and
   iv) comparing the redox status determined at step iii) with the redox status determined at step i), and determining based on said comparison if the compound has an impact on the redox status of the cell or tissue.

2. A method for screening a drug for reducing oxidative stress comprising the steps of:
   i) providing a candidate compound
   ii) contacting a cell or tissue with said candidate compound
   iii) determining the formation of disulfide-linked promyelocytic leukemia protein (PML) complexes in said cell or tissue iv) comparing the level of formation of disulfide-linked PML complexes determined at step iii) with a predetermined value, and
v) selecting the candidate compound which induces a lower level of promyelocytic leukemia protein (PML) nuclear bodies than the predetermined value.

3. A method for monitoring a treatment of a subject with a drug for reducing oxidative stress comprising
determining the redox status of a cell or tissue sample obtained from the subject by detecting the formation of disulfide-linked promyelocytic leukemia protein (PML) complexes in said cell or tissue sample and optionally, comparing said redox status with a predetermined value representing a predetermined stage of oxidative stress, the redox status of said cell or tissue with respect to the predetermined value indicating the evolution of the oxidative stress in said patient, and therefore the degree of efficacy of the treatment.

* * * * *